United States Patent

Peligrad

(10) Patent No.: US 8,934,959 B2
(45) Date of Patent: Jan. 13, 2015

(54) PHYSIOLOGICAL PHARMACOKINETIC ANALYSIS FOR COMBINED MOLECULAR MRI AND DYNAMIC PET IMAGING

(75) Inventor: Dragos-Nicolae Peligrad, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 407 days.

(21) Appl. No.: 13/000,382

(22) PCT Filed: Jun. 22, 2009

(86) PCT No.: PCT/IB2009/052679
§ 371 (c)(1),
(2), (4) Date: Dec. 21, 2010

(87) PCT Pub. No.: WO2010/004464
PCT Pub. Date: Jan. 14, 2010

(65) Prior Publication Data
US 2011/0105892 A1    May 5, 2011

Related U.S. Application Data

(60) Provisional application No. 61/079,213, filed on Jul. 9, 2008.

(51) Int. Cl.
*A61B 5/055* (2006.01)
*G01R 33/56* (2006.01)
*A61K 49/18* (2006.01)
*A61K 51/12* (2006.01)
*G01R 33/48* (2006.01)

(52) U.S. Cl.
CPC ............ *G01R 33/5601* (2013.01); *A61K 49/18* (2013.01); *A61K 51/12* (2013.01); *G01R 33/481* (2013.01)

USPC ........... 600/411; 600/420; 600/431; 600/436; 250/363.03; 250/363.04; 424/1.89; 424/9.3; 424/9.37

(58) Field of Classification Search
USPC ................. 600/410, 411, 420, 427, 431, 436; 424/1.1, 1.89, 9.3, 9.37; 250/363.01–363.04
See application file for complete search history.

(56) References Cited

U.S. PATENT DOCUMENTS 4,671,256 A  *  6/1987  Lemelson ................... 600/4
5,101,827 A  *  4/1992  Goldenberg ............. 424/1.49

(Continued)

FOREIGN PATENT DOCUMENTS

CA    2107642 A1    4/1994
WO    2005072780 A2    8/2005

(Continued)

OTHER PUBLICATIONS

Cheon, J., et al.; Synergistically Integrated Nanoparticles as Multimodal Probes for Nanobiotechnology; 2008; Accounts of Chemical Research; 41(12)1630-1640.

(Continued)

*Primary Examiner* — Ruth S Smith (57) ABSTRACT

Magnetic resonance (MR) imaging typically has excellent spatial resolution, but relatively poor temporal resolution. In contrast, positron emission tomography (PET) typically has excellent temporal resolution, but poor spatial resolution relative to MR. Resultantly, it is advantageous to use combined PET-MR imaging sequences to create hybrid or enhanced images that reap the benefits of both modalities. A contrast agent (80) that includes both a PET tracer (82) and MR contrast enhancement (86) can be used in such a combined modality setting. The contrast agent (80) also includes a targeting system (84) that allows the contrast agent (80) to pool in a region of interest.

22 Claims, 6 Drawing Sheets

(56) References Cited

U.S. PATENT DOCUMENTS

| | | | | |
|---|---|---|---|---|
| 5,377,681 | A | * | 1/1995 | Drane .................. 600/419 |
| 5,772,982 | A | * | 6/1998 | Coward ................ 424/1.73 |
| 6,226,352 | B1 | * | 5/2001 | Salb .................. 378/98.9 |
| 6,574,497 | B1 | * | 6/2003 | Pacetti ................ 600/420 |
| 7,338,651 | B2 | | 3/2008 | Bornhop et al. |
| 7,626,389 | B2 | | 12/2009 | Fiedler et al. |
| 7,657,299 | B2 | * | 2/2010 | Huizenga et al. ........ 600/410 |
| 8,038,983 | B2 | | 10/2011 | McBride et al. |
| 8,147,805 | B2 | | 4/2012 | Yang et al. |
| 2004/0138558 | A1 | * | 7/2004 | Dunki-Jacobs et al. ... 600/431 |
| 2005/0113667 | A1 | * | 5/2005 | Schlyer et al. ......... 600/411 |
| 2007/0055127 | A1 | | 3/2007 | Ladebeck et al. |
| 2007/0073143 | A1 | | 3/2007 | Siegel et al. |
| 2007/0102641 | A1 | | 5/2007 | Schmand et al. |
| 2007/0258888 | A1 | | 11/2007 | Feldmann et al. |
| 2008/0108894 | A1 | * | 5/2008 | Elgavish et al. ........ 600/420 |
| 2008/0146914 | A1 | | 6/2008 | Polzin et al. |
| 2008/0319304 | A1 | * | 12/2008 | Declerck et al. ........ 600/411 |
| 2009/0030304 | A1 | * | 1/2009 | Feiweier et al. ........ 600/411 |
| 2009/0220431 | A1 | | 9/2009 | Cheon et al. |

FOREIGN PATENT DOCUMENTS

| | | |
|---|---|---|
| WO | 2006074272 A2 | 7/2006 |
| WO | 2006111869 A2 | 10/2006 |
| WO | 2007042504 A2 | 4/2007 |

OTHER PUBLICATIONS

Flacke, S., et al.; Novel MRI Contrast Agent for Molecular Imaging of Fibrin: Implications for Detecting Vulnerable Plaques; 2001; Circulation; 104:1280-1285.

Gustafsson, B., et al.; A Novel Dual-Modality MRI/PET Probe; 2006; Proc. Intl. Soc. Mag. Reson. Med.; 14:1888.

Jarrett, B. R., et al.; Synthesis of 64 Cu-Labeled Magnetic Nanoparticles for Multimodal Imaging; 2008; Bioconjugate Chem; vol. 19: 1496-1504.

Lewin, M., et al.; Tat peptide-derivatized magnetic nanoparticles allow in vivo tracking and recovery of progenitor cells; 2000; Nature Biotechnology; vol. 18:410-414.

Lanza, G. M., et al.; Molecular Imaging in MR with Targeted Paramagnetic Nanoparticles; 2003; MedicaMundi; 47(1) 34-39.

Tofts, P. S.; Modeling Tracer Kinetics in Dynamic Gd-DTPA MR Imaging; 1997; Journal of Magnetic Resonance Imaging; 7:91-101.

Tofts, P. S., et al.; Measurement of the Blood-Brain Barrier Permeability and Leakage Space Using Dynamic MR Imaging 1. Fundamental Concepts; 1991; Magnetic Resonance in Medicine; 17:357-367.

Wong, K-P., et al.; Simultaneous Estimation of Physiological Parameters and the Input Function-In Vivo PET Data; 2001; IEEE Trans. on Information Technology in Biomedicine; 5(1)67-76.

Nahrendorf, M., et al.; Nanoparticle PET-CT Imaging of Macrophages in Inflammatory Atherosclerosis; 2008; Circulation; 117:379-387.

\* cited by examiner

PHYSIOLOGICAL PHARMACOKINETIC ANALYSIS FOR COMBINED MOLECULAR MRI AND DYNAMIC PET IMAGING

CROSS REFERENCE TO RELATED APPLICATIONS

This application claims the benefit of U.S. provisional application Ser. No. 61/079,213 filed Jul. 9, 2008, which is incorporated herein by reference.

The present application relates to the diagnostic imaging arts. It finds particular application with hybrid positron emission tomography-magnetic resonance (PET-MR) systems, and will be described with particular reference thereto. It is to be understood, however, that the present application is applicable to other hybrid systems but is not limited to hybrid systems. Rather it can be used in sequential PET and MR scans from stand-alone or co-axial scanners, or other systems, and is not limited to the aforementioned application.

Both PET and MRI suffer from inherent limitations. Dynamic PET (dPET) imaging provides a direct detection of the concentration of a contrast agent with a high temporal resolution of functional and metabolic information combined with a high sensitivity of the PET tracer detection. One drawback is that it often suffers from a low quantification precision of physiological, functional, and morphological parameters of tumors, etc. In contrast to dPET, the measured signal detected by dynamic contrast enhanced (DCE) MRI depends on the pulse sequences used for detection, that is, on the T1 and T2 relaxation rates. There might not always be a linear dependence on the contrast agent concentration. The concentration of the contrast agent is not a direct observable of the experiment, and is typically extracted numerically for most cases. Additionally, the time resolution is typically limited to several seconds, which can be insufficient for some fast relaxation processes. MR has relatively high spatial resolution, and PET has relatively high temporal resolution. Resultantly, PET and MR systems are used in conjunction with each other, as the two modalities can complement each other.

As the two modalities use significantly different imaging techniques, different vehicles are used either to produce an image or to aid in imaging. In PET, the actual substance that is imaged is taken up by the tissue of interest, and is imaged while it is there. In MR imaging, the tissue is excited and imaged directly, while contrast agents can be used to help distinguish between tissue of interest and the surrounding vasculature. Typically, the MR contrast agent is not taken up by the tissue of interest, but rather flows freely in the bloodstream until it eventually filtered out. In combined PET/MR studies, it is typical to inject both the MR contrast agent and the PET radiopharmaceutical prior to the scan, both of which are hard on a patient's kidneys and liver.

In certain applications, such as with imaging cancerous tumors or arterial plaque, the area of interest is readily accessible by blood. As tumors grow, new blood vessels are created to accommodate the growth. In such situations, MR contrast agents can be used to highlight the tissue of interest instead of distinguishing the tissue of interest from the surrounding vasculature. In order to do so, however, it must settle and anchor on the tissue of interest, so that it may aid in imaging.

Biopsies are often uses to garner information about a sampled tissue. They can be used to gain information about the microvascular biology, but can only provide an incomplete view of such vasculature. Biopsies are sometimes subject to sampling errors, and in the case of cancerous tissues, run the risk of stimulating metastatic activity.

The present application provides a new and improved contrast agent and radiopharmaceutical, and method and apparatus for usage, which overcomes the above-referenced problems and others.

In accordance with one aspect, a contrast agent is provided. The contrast agent includes a first component that is able to be imaged by a magnetic resonance imaging apparatus. A second component of the contrast agent includes a radiopharmaceutical that is able to be imaged by a nuclear imaging apparatus. The contrast agent also includes a targeting system that takes advantage of biological processes to cause the contrast agent to collect in a target region.

In accordance with another aspect, a method of diagnostic imaging is provided. A subject is injected with a contrast agent that is able to be imaged by both magnetic resonance imaging and positron emission tomography. Magnetic resonance is excited in selected dipoles of the subject and the contrast agent. The magnetic resonance is detected. Radiation indicative of radioactive decay events of the contrast agent are detected with a detector array. At least one of the detected magnetic resonance and the radiation is reconstructed into an image representation of the subject. The image representation is displayed.

One advantage lies in improved overall signal to noise ratio.

Another advantage lies in the symbiotic combination of kinetic parameters obtained from high temporal resolution with spatially resolved 3D anatomical and morphological data.

Another advantage lies in augmentation of vascular visualization with time data.

Another advantage lies in extended kinetic and functional processing of combined PET-MR data by software and modeling tools.

Another advantage lies in improved 4D matching of PET and MR images using dynamic PET to obtain time specific data.

Another advantage lies in application to angiogenesis and cardiology.

Another advantage is that the need to halve the doses of contrast agent administered to the subject for a combined PET/MR scan is eliminated.

Another advantage lies in early detection of cancer, and treatment monitoring.

Another advantage lies in non-invasive diagnosis of neovasculature.

Another advantage lies in improved biocompatibility of the contrast agent with the patient.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

The present application can be used in cardiology studies, for example, in angiography, ischemia, and myocardium examinations, or diagnosis of vulnerable plaques. It also finds application in oncology, for the quantification of angiogenesis. Angiogenesis is the process of new blood vessel growth that occurs in a variety of physiological states. Tumors have the ability to stimulate endothelial cell growth, and thus, angiogenesis becomes a key pathway for tumor growth, invasion of surrounding healthy tissues, and metastatic activity. As solid tumors require access to the bloodstream to metastasize to secondary sites around the body, tumor blood vessels are an important parameter and target for cancer therapy.

The vascular endothelial growth factor has an important role in stimulating angiogenesis. Tumor growth beyond the size of about 2 $mm^3$ requires assembly of a neovascular network. There is a clear correlation between angiogenic growth and prognosis in tumors, such as breast cancer, prostate cancer, and colo-rectal cancer tumors. Tumors respond positively to angiogenic inhibitors that target the vascular endothelial growth factor pathways. The present application aids in the understanding of the molecular pathways underlying angiogenesis and the identification of candidate drugs for treatment.

Treatment often includes destruction of existing vascular network around a tumor and prevention of new vessel formation. That is, both antivascular and antiangiogenic agents have value in tumor treatment. The inhibition of angiogenesis is one of the most promising strategies that can support cancer therapies. The presently described multi-modality detection allows early diagnosis, therapy monitoring, and therapy follow up of such therapy.

Figure 1:
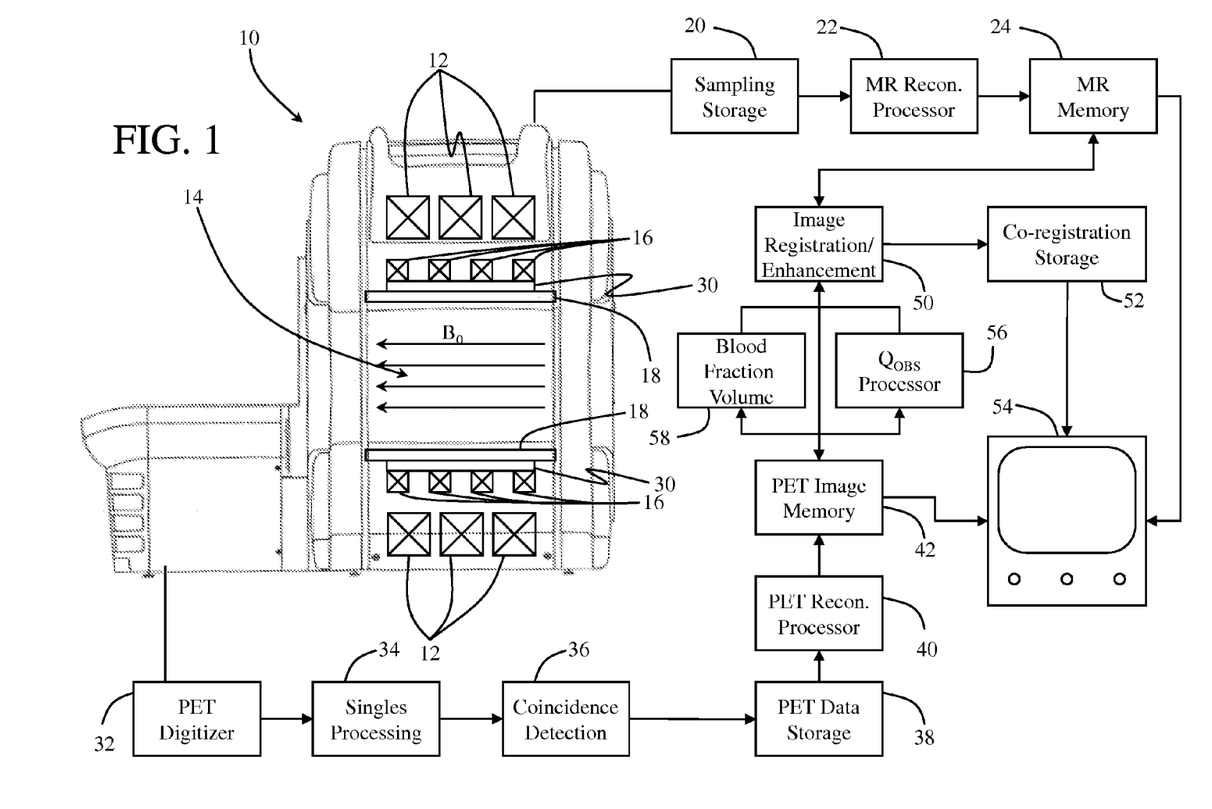
FIG. 1 is a diagrammatic illustration of a combined PET/MR scanner, in accordance with the present application.

With reference to FIG. 1, an embodiment of a combined or hybrid magnetic resonance (MR) and PET data acquisition system 10, which generates intrinsically aligned PET and MR images is depicted. It is to be understood that a multimodality system is ideal for temporally and spatially aligned images; images taken from different scanners that are remotely located or spatially displaced are also contemplated, and similarly viable. The illustrated scanner 10 is an integrated system, but other scanner orientations are equally plausible, such as side-by-side systems, insert systems, co-axial systems, and the like. The magnetic resonance scanner shown includes an annular magnet 12 including a plurality of conductor coil windings 16 (diagrammatically depicted in FIG. 1 by boxes with crossing lines) that generate a static magnetic field $B_0$ within an imaging region 14. The magnet 12 may be superconducting or resistive in nature; in the former case the magnet 12 is typically disposed in a cryogenic dewar or other cooling system (not shown). The illustrated magnet 12 is a solenoidal magnet having a relatively horizontal $B_0$ field through the imaging region 14. Though the polarity of the $B_0$ field is shown right to left, the opposite polarity is also suitable. In other embodiments, the magnet 12 may have a C or other configuration oriented to produce a vertical or otherwise oriented static magnetic field.

The magnetic resonance scanner also includes a magnetic field gradient assembly, which in the illustrative embodiment of FIG. 1 includes gradient coil windings 16 that cooperatively superimpose magnetic field gradients on the static $B_0$ magnetic field responsive to selective energizing of selected gradient coil windings 16. Optionally, the magnetic field gradient coil, magnet, or both may include other features not shown for forming, stabilizing, and dynamically adjusting the magnetic field, such as passive ferromagnetic shims, active shimming coils, and the like. The magnetic resonance scanner further includes a radio frequency excitation and reception system. The radio frequency system includes at least one component, such as an illustrated whole body radio frequency coil 18, which can be energized at a suitable radio frequency to excite magnetic resonance in a subject disposed in the imaging region 14. The coil 18 can also operate as a radio frequency receiver to receive or detect magnetic resonance emanating from the imaging region 14 after RF excitation. In some embodiments, different coils are used for the excitation and reception operations. For example, the built-in coil 18 may be used to excite magnetic resonance, and a different, local coil or dedicated receive coil (not shown) may be positioned over, on, or close to the subject in the imaging region 14 to detect magnetic resonance. The radio frequency system in one embodiment is tuned to the resonance frequency of $^1H$ and in another embodiment is tuned to the resonance frequency of $^{19}F$. The radio frequency system can be dual tuned for concurrent or sequential $^1H$ and $^{19}F$ imaging. It is contemplated for the same magnetic resonance scanner to be configurable in different ways using different combinations of built-in coils, local coils, or both.

The gradient assembly and the radio frequency system work together to induce magnetic resonance with an imaging sequence, such as one of the fast imaging sequences, e.g. a gradient echo sequence, a fast spin echo, etc. Faster imaging systems maximize MR temporal resolution. Received magnetic resonance samples are stored in a magnetic resonance sampling storage 20. A magnetic resonance reconstruction processor 22 applies a suitable reconstruction algorithm to reconstruct the magnetic resonance samples to form a reconstructed image or series of temporally incremented images that is/are stored in a magnetic resonance image memory or buffer 24. The reconstruction processor 22 applies a reconstruction algorithm that comports with the selected spatial encoding used in generating the magnetic resonance data. For example, a Fourier transform reconstruction algorithm may be suitable for reconstructing Cartesian encoded magnetic resonance data. Optionally, part of the MR reconstruction may be done in-line, before data storage and completion of reconstruction.

With continuing reference to FIG. 1, the illustrated combined or hybrid MR and PET data acquisition system 10 further includes radiation detectors for performing PET data acquisition. In the illustrative example of FIG. 1, an annular array of radiation detectors 30 encircles the bore of the hybrid system. The illustrated array 30 includes a scintillator layer and a layer of electron multiplier based photon detectors, however, other detector configurations such as planar detector arrays disposed about the imaging region 14 are contemplated. Solid state radiation detectors and solid state optical detectors are also contemplated. The radiation detector array 30 is configured to detect 511 keV gamma rays that are emitted by positron/electron annihilation events. In PET data acquisition, two substantially simultaneous 511 keV gamma ray detection events are presumed to have originated from the same positron/electron annihilation event, which is located somewhere along a "line of response" (LOR) connecting the two substantially simultaneous 511 keV gamma ray detection events. This line of response is also sometimes called a projection or a ray, and the collected PET data is referred to as projection data.

In conventional PET, substantially simultaneous 511 keV gamma ray detection events are defined as two 511 keV gamma ray detection events occurring within a selected short time window, such as within four nanoseconds of each other. Any positron annihilation that does not occur at the center of the field of view (FOV) will have a small difference in time of arrival at the opposing detector elements, proportional to the difference in travel times for the gamma rays, about four nanoseconds at the edge of the FOV. A related technique, called time of flight PET or TOF-PET, takes advantage of this small time difference to further localize the positron/electron annihilation event along the LOR with sub nanosecond precision.

The radiation detector array 30 of the hybrid system 10 is used to acquire PET or TOF-PET data. The gamma ray detection events are processed by a PET digitization unit 32 that performs time to digital conversion (TDC) and analog to digital conversion (ADC) of detection events, and a singles processing unit 34 that performs clustering, energy estimation, time stamping, and positioning. The singles processing unit 34 optionally filters out detections that are outside of a selection energy window for the expected 511 keV gamma ray energy. In some embodiments, the radiation detectors are pixelated. In other embodiments, clustering is applied by a block readout algorithm such as Anger logic or the like to provide further spatial localization refinement of the gamma ray detection events defining the projection. A coincidence detection processor 36 employs temporal windowing to identify gamma ray detection events that occurred substantially simultaneously, and hence likely correspond to a common positron/electron annihilation event and hence define a projection or line of response.

For TOF processing, the time difference between the identified substantially simultaneous or coincident detection events is used to spatially estimate the positron/electron annihilation event along the line of response.

The resulting PET or TOF-PET data are stored in a PET data storage 38. It is to be understood that the PET data could be stored before or after coincidence determination. A PET reconstruction processor 40 processes the LORs or localized projection data using a suitable reconstruction algorithm to generate a series of temporally incremental reconstructed images that are stored in a PET image storage or buffer 42. In one embodiment, the PET data is stored in a list mode, i.e. each LOR is stored with a time stamp. This enables a temporal window(s) to be adjusted in the data such that each reconstructed image falls in a selected and adjustable time window.

The MR and PET acquisitions are optionally performed concurrently. This allows the superior spatial resolution of the MR scan to be enhanced by the superior temporal resolution of the PET scan, creating a 4D representation that is more complete than a representation that either modality could produce on its own. Alternatively or additionally, MR and PET acquisition can be done sequentially (e.g., MR first followed by PET, or vice versa) or can be interleaved. An image registration and enhancement processor 50 spatially registers and, optionally, temporally registers the reconstructed MR and PET images. The co-registered images are stored in a co-registration image memory or buffer 52. Additionally, the individual PET or MR images can be enhanced with the other modality, and can be stored in the respective memory 24, 42. The images so registered or enhanced are suitably displayed on a display device 54, rendered using suitable two- or three-dimensional rendering software, or otherwise processed.

One advantage of accurately knowing the molecular biochemical processes that underlie medical images is being able to characterize certain tissue types, e.g. cancer, in a non-invasive, in vivo setting. Dynamic contrast enhanced (DCE) MRI provides a visual representation of both the anatomy and microvascular biology of a cancerous tumor by measuring temporal changes in the MR signal intensity associated with the intravascular injection of a contrast agent. Spatial heterogeneity in the kinetics of the contrast agent is assumed to reflect variations in tissue perfusion, microvascular permeability, and the creation of new blood vessels to accommodate growing tumors (angiogenesis). Angiogenic microvessels support growing cancer cells. Such microvessels are identifiable in part by larger endothelial cell formations resulting in a higher permeability to small molecules. Gadolinium ($Gd^{3+}$) is a small molecule MR contrast agent currently in use. $Gd^{3+}$ can pass from vascular space into interstitial extracellular space, but does not pass cell membranes. The rate at which $Gd^{3+}$ passes to extracellular space is dependent on tumor perfusion and capillary permeability. As $Gd^{3+}$ can pool in extracellular spaces, it is useful in identifying neovascular developments associated with malignant tumor growth.

In PET, it is difficult to resolve the heterogeneity within a given volume of interest (V) because of the relatively low spatial resolution of PET. In dynamic PET (dPET) the subject is typically injected and data points are taken with their associated time stamps. After some time delay, more data points are taken with time stamps. Thus, a 4D set of data is acquired as the tracer progresses to the region of interest. The total activity within a voxel ($Q_{OBS}(t)$) measured in dPET is a unique attainable observable to dPET. $Q_{OBS}(t)$ is observable in extracellular, extravascular space ($V_{EES}$) and it can be calculated by:

$$Q_{OBS}(t) = V_{EES}C_{OBS}(t) = (1-\beta)V_{EES}[C_{EES}(t) + C_T(t)] + \beta V_{EES}C_P(t)$$

where $\beta$ is the blood volume fraction of the vascular structure, $C_P(t)$ is the plasma input function, $C_T(t)$ is the concentration of imaging agent that is specifically bound in the voxel, and $C_{EES}(t)$ is the imaging agent in the region that is not specifically bound. The vascular term $\beta V_{EES}C_P(t)$ plays a significant role in parametric map estimation, and may lead to systematic errors if neglected. The total activity $Q_{OBS}$ is calculated by a processor 56.

In addition, the plasma input function representing the concentration of free, unbounded imaging agent needed for a reliable pharmacokinetic analysis is not necessarily given by the activity measured directly from the left heart ventricle since this may not represent only the amount of free contrast agent in the blood plasma. However, the MRI contrast agent is not bound to blood plasma, and is not able to pass the blood/tissue barrier. Resultantly, it may be treated as a purely extracellular blood pool marker.

A reliable quantification of imaging agent kinetic is desirable in order to better quantify physiological parameters of lesion tissues, such as blood vessel permeability, blood flow, and blood leakage volumes. DCE-MR and 19F-MR both yield additional morphological information about the vascular makeup within the voxel. From this additional information, a combined detection of the dPET and MR modalities can add an extra observable, that is, the blood volume fraction 58 of the total measured activity (as measured by dPET).

This extra information about the vascular makeup can be very useful in cancer staging and treatment. Generally, the more vast the vascular network around a tumor site, the more advanced the tumor is. More advanced tumors often develop necrotic cores that are of the same cellular makeup as the rest of the tumor, but the cells in these cores have all but stopped any metabolic activity or replication. Such cores are all but impervious to treatment, as typical treatments rely on the overly-prolific nature of cancer cell duplication. By knowing the makeup of neovascular networks that have developed around such cores and are supplying the surrounding cancerous tissue, treatable tissues (such as rapidly duplicating cancer cells and the neovasculature itself) can be identified and targeted as part of a treatment regimen.

Another advantage of the combination of dPET and MR is significantly improved signal to noise ratio allowing, for example, partial volume corrections. A combined sequence using both modalities and a common, extracellular tracer successfully combines the high spatial resolution of the MRI modality, and the high time resolution of dPET.

In one embodiment, the combined tracer uses a targeted molecule, which has a payload of DCE-MR or MR contrast agent (such as $Gd^{3+}$ or $^{19}F$) and a PET tracer (such as $^{18}F$.)

Figure 2:
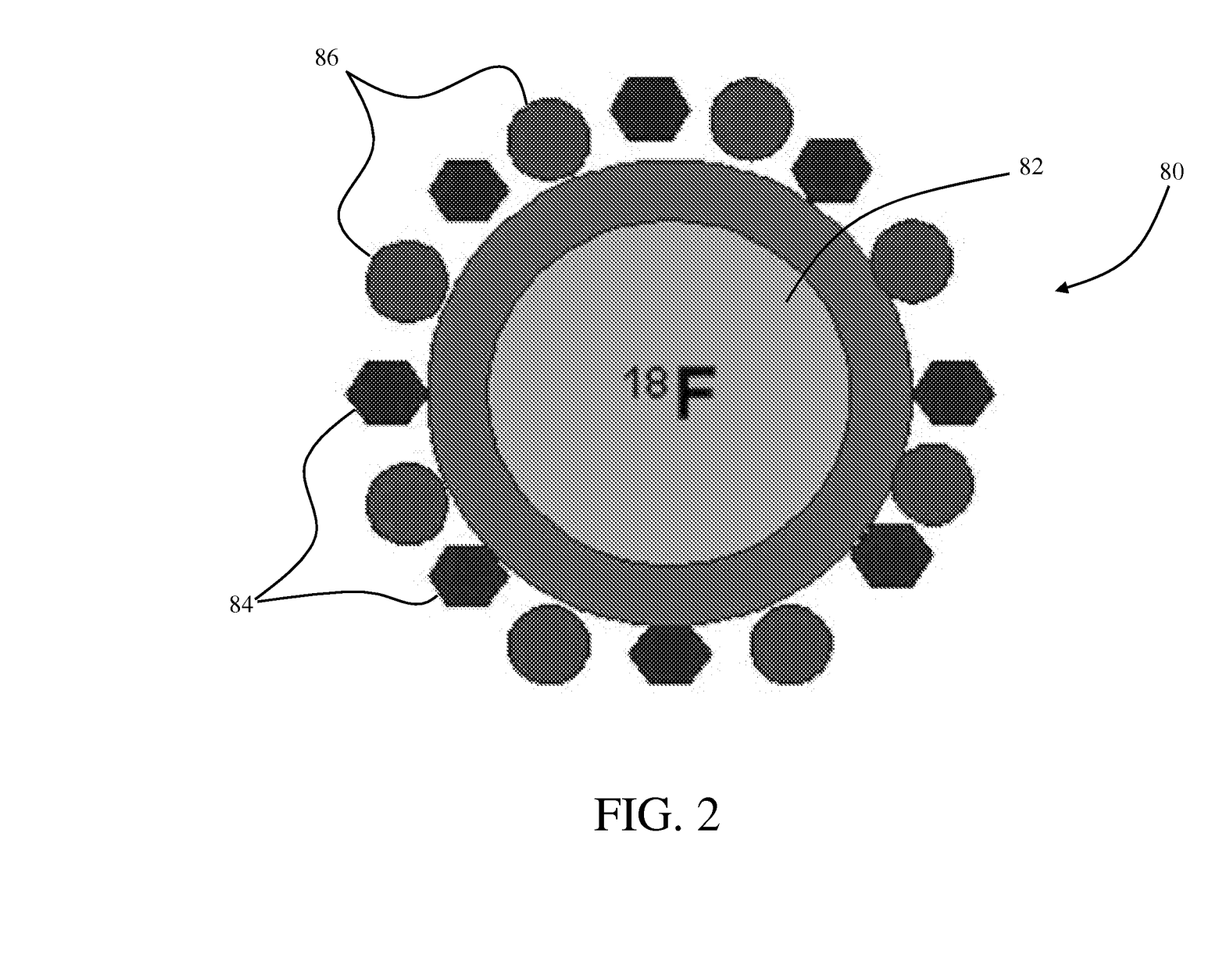
FIG. 2 is one embodiment of a combined PET/MR contrast agent.

The application now turns to several embodiments of a dual PET/MR contrast agent. One embodiment of a contrast agent facilitates both a dPET and a DCE-MRI or 19F-MRI signal. As shown in FIG. 2, the contrast agent includes a molecule 80. The molecule 80 includes a carrier 82 that is the radioactive PET tracer. In the present embodiment, the carrier is $^{18}F$. The molecule 80 also includes a targeting system 84. The targeting system 84 is what allows the molecule 80 to gather in the region of interest. Possible candidates for the targeting system 84 are monoclonal antibodies, adaptamers, peptidomimetics, polysaccharides, and the like. The molecule also includes a payload 86, which includes a DCE-MRI contrast agent, such as $Gd^{3+}$. Other payloads such as drugs are also contemplated. The embodiment of FIG. 2 includes both a DCE-MRI contrast agent and a dPET tracer, making it suitable for a combined dPET/DCE-MRI imaging procedure. Typically, in a combined PET/MR scan, the doses of contrast agent and PET tracer would have to be halved, so as not to be an excessive burden on the subject's kidneys and liver. Since the subject was being administered two substances, only half of each could be given. By combining the tracers, the subject can be given the equivalent of a full dose of each, without actually doubling the workload on the subject's kidneys and liver. This leads to an overall improvement of signal to noise ratio.

Figure 3:
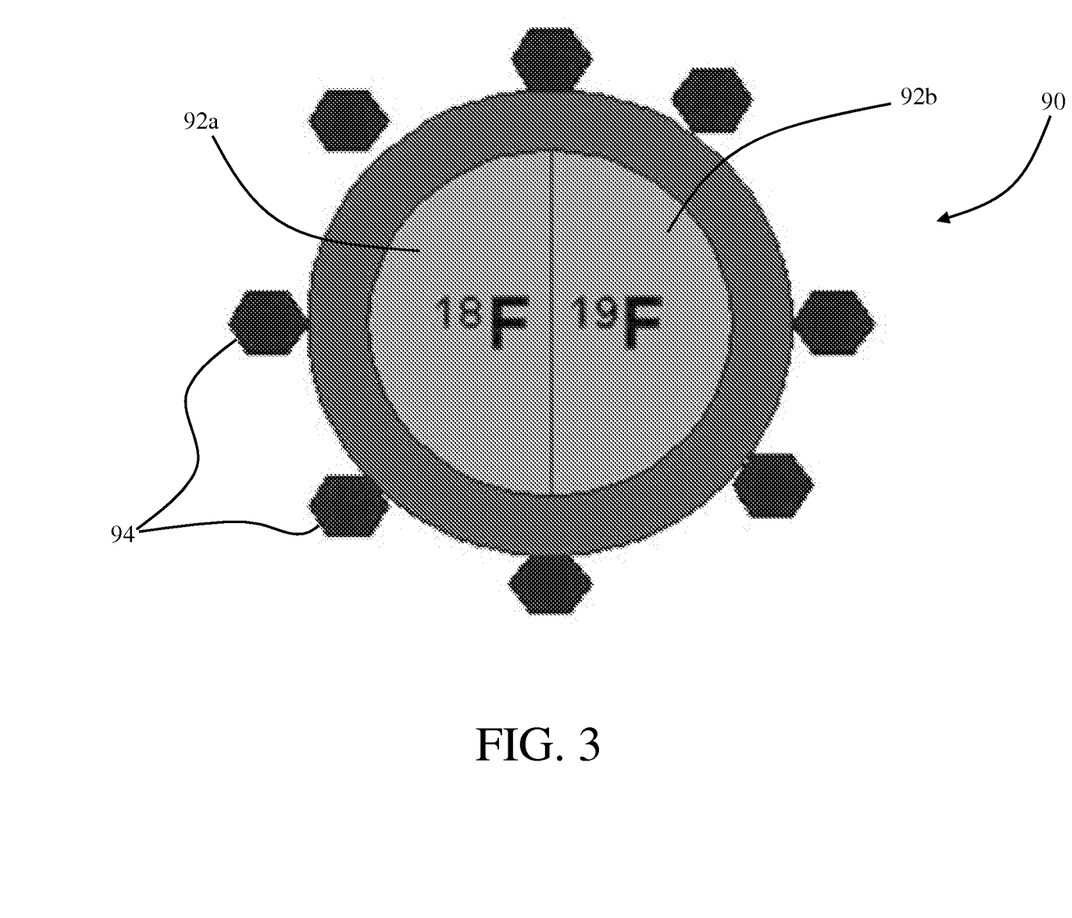
FIG. 3 is another embodiment of a combined PET/MR contrast agent.

In another embodiment, as shown in FIG. 3, another contrast agent molecule 90 is depicted. In this embodiment, the molecule 90 includes a carrier 92 that has both a radioactive PET tracer 92a (such as $^{18}F$) and a 19F-MRI tracer 92b, which is $^{19}F$. The molecule 90 also includes a targeting system 94 similar to the targeting system 84 of the molecule 80 of FIG. 2. The molecule 90 of FIG. 3 would be suitable for a dPET/19F-MRI imaging procedure.

Figure 4:
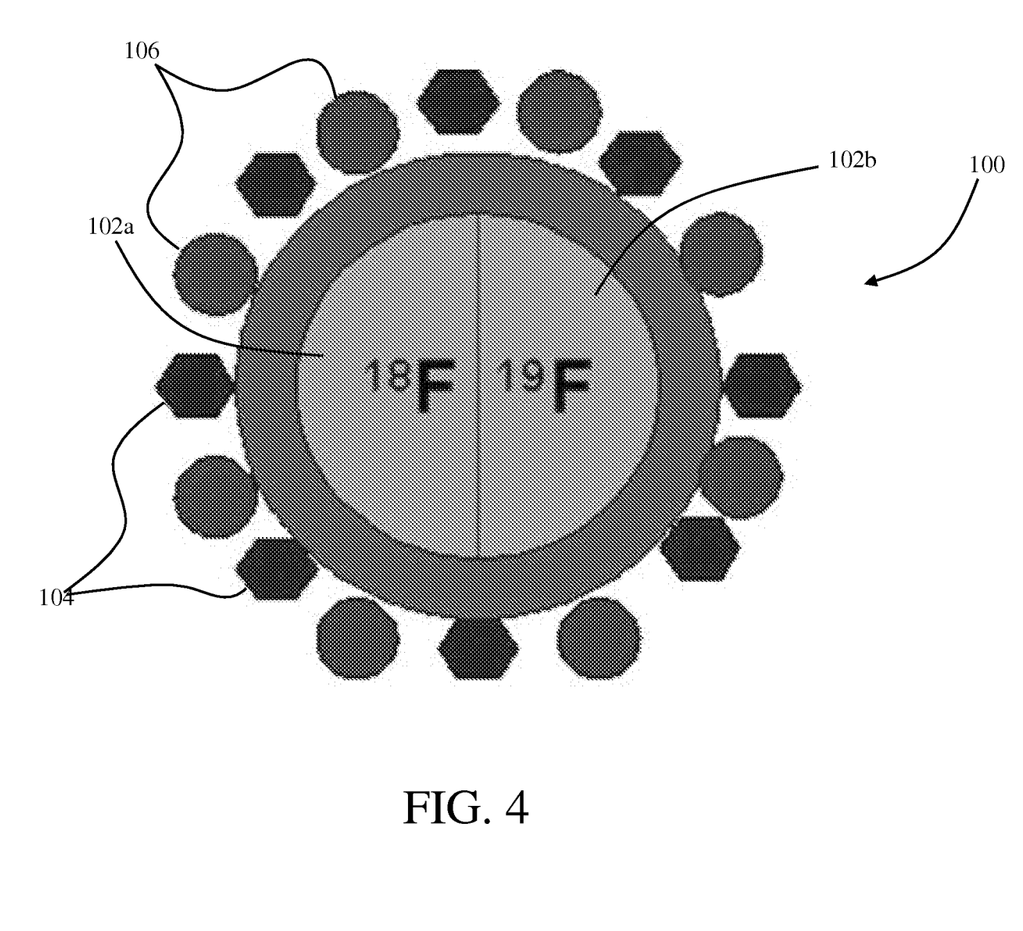
FIG. 4 is another embodiment of a combined PET/MR contrast agent.

With reference now to FIG. 4, another embodiment of a molecule 100 is depicted. Like the molecule 90 the molecule 100 has a combined carrier 102 that includes both a PET tracer 102a ($^{18}F$) and a 19F-MRI contrast agent 102b ($^{19}F$). Additionally, the molecule 100 includes a targeting system 104, similar to the previous embodiments. This embodiment also has a payload 106 of DCE contrast agent. Thus, the embodiment of FIG. 5 is suitable for either a dPET/19F-MRI imaging procedure, or a dPET/DCE-MRI imaging procedure.

Figure 5:
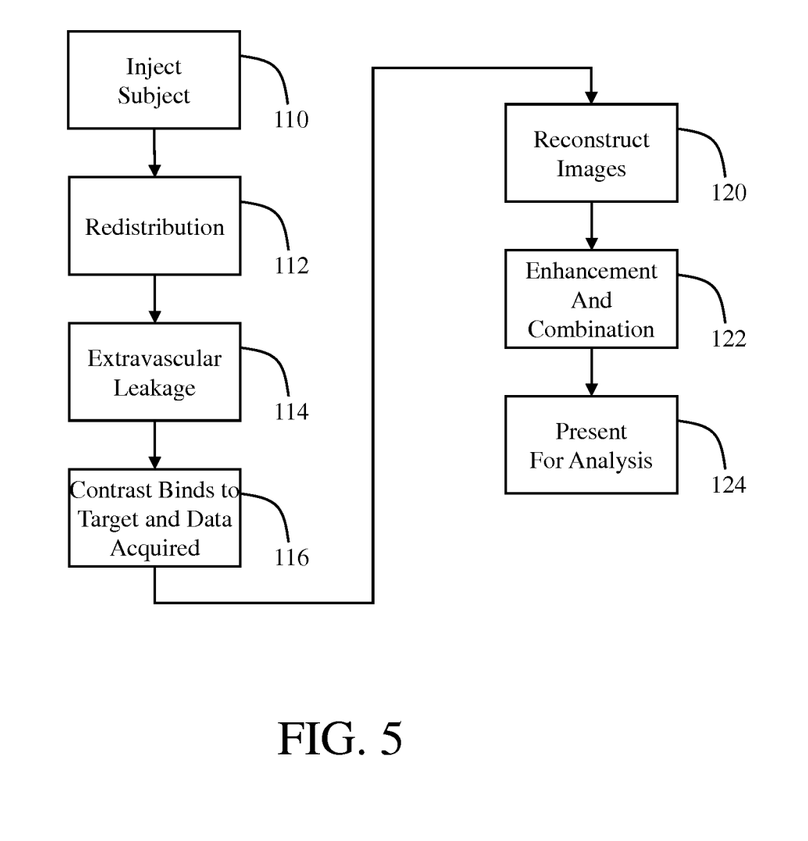
FIG. 5 is a flow diagram representative of a PET/MR image acquisition.

With reference now to FIG. 5, the contrast agent as previously described is injected 110 into the subject. The properties of the constituent components of the contrast agent are known. It can be expected with relative certainty that the contrast agent will remain outside the cells, and be a pure blood pool marker that does not enter erythrocytes, does not bind to blood plasma proteins, and is not able to pass through the blood-tissue barrier. After injection, the contrast agent redistributes 112 through the vascular system until it reaches the region of interest, such as a lesion caused by tumor cells. Near the lesion the contrast agent leaks out 114 through damaged capillary walls into the interstitial region, a region both extracellular and extravascular. After some amount of time, the contrast agent binds 116 to its target.

Concurrently, an image data acquisition is performed. In dPET, data is continuously gathered over time, or gathered in sequential time steps so that the development of the contrast agent over time can be observed. This is in contrast with static PET, where the tracer is allowed to settle in the region of interest, and data acquisition begins after the tracer has already arrived. In one embodiment, the PET and the MR acquisitions are performed simultaneously. This is so the timing data gathered from the PET acquisition may be applied to the MR data. The respective images are then reconstructed 120. Next, the images are used to complement each other. One or both of the acquired images is enhanced 122 by data from the other image. This step may also include creating a hybrid PET-MR image. Lastly, enhanced or hybrid data are presented 124 to the user for analysis. In one embodiment, the user can select which images to view, e.g. originals or hybrids, relative weighting of the PET and MR images, and decide whether additional enhancements are desired. Data may also come in the form of parametric maps, illustrating flow gradients of $k_1$, $k_2$, $k_3$, and $k_4$. The user could also view volume fraction maps of the region, or time activity curves illustrating the behavior of the contrast agent as a function of time.

This physiological process can be described mathematically following a compartmental approach. The distribution of the contrast agent in the patient is now traced simultaneously by a dPET and an MRI modality over the same period of time. Measuring the same quantity, namely the concentration of the contrast agent simultaneously with different complementary modalities improves the overall signal to noise characteristics of the signal since the different modalities produce different noise patterns.

Figure 6:
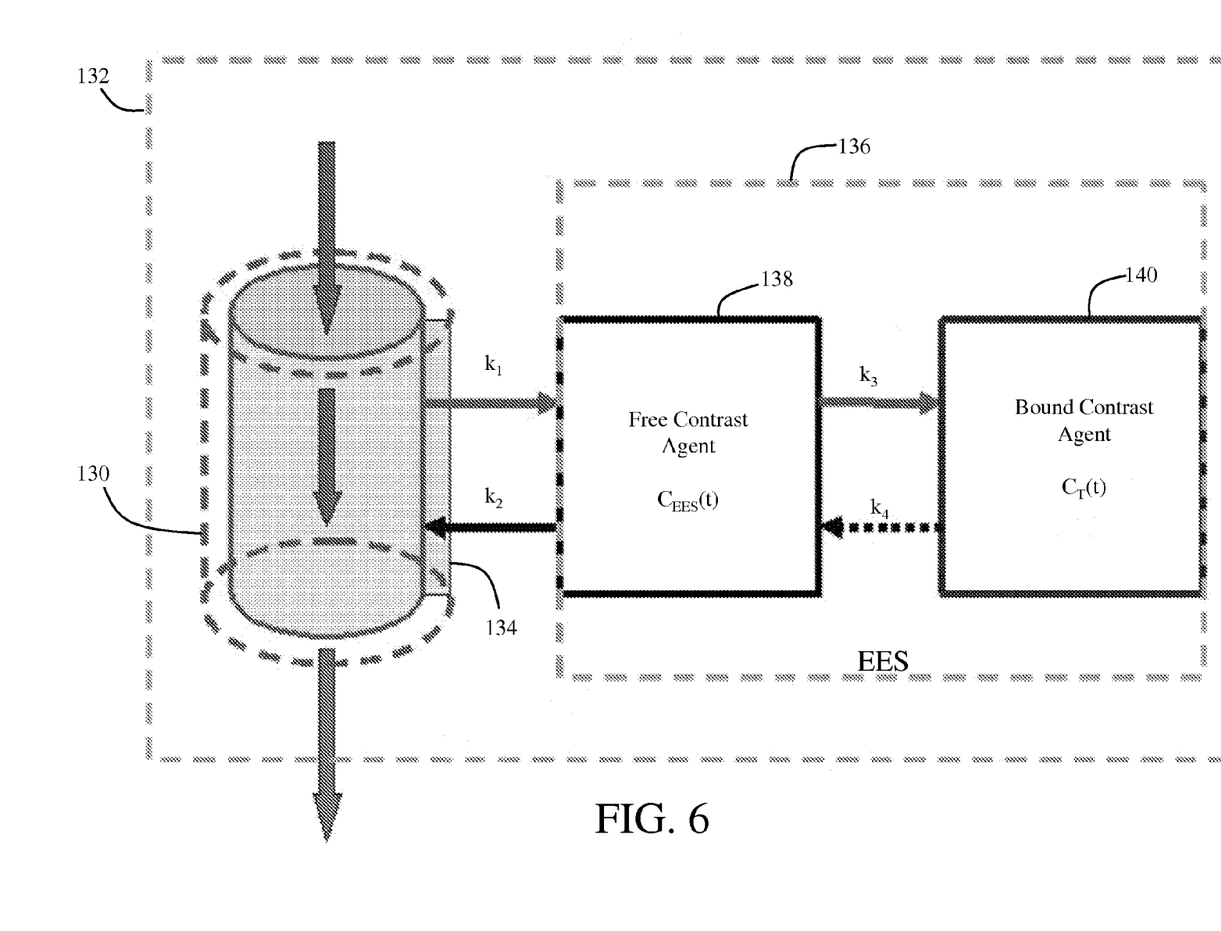
FIG. 6 shows blood flow patterns in a region of interest.

With reference to FIG. 6, the contrast agent flows with the blood through a capillary 130 that is located in a voxel of interest 132. The inner wall of the capillary 130 is represented by a solid line, while the outer wall is represented by a dotted line. The contrast agent can pass through the endothelium 134 of the vessel into an extravascular, extracellular space (EES, $((1-\beta)V))$ 136. The flow from the capillary 130 into the EES 136 is represented by $k_1$. Conversely, flow from the EES 136 into the capillary 130 is represented by $k_2$. Within the volume $V_{EES}$ of the EES 136 the contrast agent can be free 138, that is, not specifically bound to any object, represented by $C_{EES}(t)$. The contrast agent within the EES 136 can also be bound to the surface of the target tissue 140, represented by $C_T(t)$. The change of the contrast agent from an unbound state 138 to a bound state 140 within the EES 136 is represented by $k_3$, and the change of the contrast agent from a bound state 140 to an unbound state 138 within the EES 124 is represented by $k_4$. In other words, $k_1$ is indicative of the contrast agent perfusion, while $k_3$ indicates uptake in the region. By knowing the kinetic rates, the resolution in the parametric maps can be improved, that is, more information is known about the contrast agent kinetic in space. This results in an overall improvement of spatial resolution of the PET/MR system.

The mathematical description of the compartmental topology of FIG. 6 can then be described by the following linear differential equations:

$$\frac{dC_{EES}(t)}{dt} = -(k_2 + k_3)C_{EES}(t) + k_4 C_T(t) + \frac{k_1 C_P(t)}{V_{EES}}$$

$$\frac{dC_T(t)}{dt} = k_3 C_{EES}(t) - k_4 C_T(t)$$

which can be solved as shown in the calculation of $Q_{OBS}(t)$, above. By using concurrent data to solve these equations, a step is eliminated.

These calculations are used to quantify the dynamic changes in the state of the contrast agent. For example, when unbound contrast agent stops becoming bound in the EES $$\text{i.e. } \frac{dC_T(t)}{dt} \text{ approaches zero}$$

it can indicate that the target tissue in the EES is saturated. In ongoing treatment, the total activity $Q_{OBS}(t)$ can be monitored across several scans. A steady decline of $Q_{OBS}(t)$ can be an indicator of successful treatment, that is, that targeted neovasculature is being successfully destroyed or stunted. Kinetic parameter estimation involves adjusting a best guess of the parameter until the model output best matches the measured time dependent observable. Typically, the model output does not depend on the parameters in a linear fashion. A non-linear optimization approach is typically used for model fitting, such as a standard Marquardt-Levenberg algorithm. Errors in estimating rate constants can be minimized by allowing $\beta$ to be adjustable during model fitting. This uncertainty can be eliminated by taking advantage of the high spatial sensitivity offered by the simultaneous MR imaging with the PET imaging. The supplementary information can in turn be used to determine the amount of contrast agent bound within the blood volume. Therefore, considering $\beta$ as a known parameter determined separately from the MR scans limits the parameter space of possible numerical solutions to a smaller subset.

The supplementary information about the physiological parameters involved in the pharmacokinetic agent allows for a more accurate quantification of the kinetic parameters. The weighted sum of the bound 140 and unbound 138 contrast agent portions is observable and can be quantified as $Q_{OBS}(t)$ due to the high spatial resolution of the MR image. Highly resolved 3D parameter maps can be obtained which can lead to correlations between kinetic parameters and morphology, which can be of clinical value for diagnostics, therapy monitoring, and therapy follow up.

The above-described multi-modality detection enables more morphological insight and improves parametric estimation in pharmacokinetic modeling. The possibility of obtaining combined information with both high temporal resolution, and high spatial resolution enlarges the number of attainable observables by restricting parameter space to a subset corresponding to physiologically relevant values improving model identifiability and physiological relevance of the kinetic parameters.

Another possible application of the present dual modality contrast agent is in cardiology, as the targeting system can be geared to target and adhere to plaque buildup in a subject's arteries.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A diagnostic imaging apparatus for contrast enhanced imaging of a patient, the apparatus comprising:
    a magnetic resonance imaging apparatus including:
        a main magnetic coil assembly for generating a main magnetic field in an imaging region of the apparatus,
        a gradient coil assembly for overlaying gradient magnetic fields on the main magnetic field, and
        an RF coil assembly for at least transmitting RF signals into the imaging region and receiving magnetic resonance signals from the imaging region;
    a nuclear PET imaging apparatus including:
        a detector array configured to detect nuclear decay events concurrently with the receiving of the magnetic resonance signals by the RF coil assembly, and
        at least one reconstruction processor for producing an image representation from the nuclear decay events detected by the detector array that gather in the imaging region and from the detected magnetic resonance;
    a common PET and MRI agent configured for injection into a patient disposed in the imaging region, the common agent including:
        a carrier including a fluorine-19 component which is imaged by the magnetic resonance imaging apparatus and a radiopharmaceutical which includes fluorine-18 which decays to generate the nuclear decay events detected by the PET imaging apparatus, the fluorine-18 being imaged concurrently with the imaging of the fluorine-19 component by the magnetic resonance imaging apparatus,
        a targeting system that takes advantage of biological processes to cause the common agent to collect in a target region, and
        an MRI contrast agent that is imaged by the magnetic resonance imaging apparatus.

2. The diagnostic imaging apparatus as set forth in claim 1, wherein the common agent is able to pass through a capillary endothelium, but unable to pass into a cell.

3. The diagnostic imaging apparatus as set forth in claim 1, wherein the targeting system includes at least one of a monoclonal antibody that attaches to a certain type of cell wall and a fibrin-specific paramagnetic nanoparticle, and the common agent is able to pass through a capillary endothelium, but unable to pass into a cell.

4. A method of diagnostic imaging comprising:
    injecting a subject with a common PET/MRI agent including:
        a first component including fluorine-19 that is imaged by a magnetic resonance imaging apparatus,
        a second component that includes a radiopharmaceutical including fluorine-18 that is imaged by a PET imaging apparatus concurrently with the imaging of the first component by the magnetic resonance imaging apparatus,
        a targeting system that takes advantage of biological processes to cause the common agent to collect in a target region, and
        an MRI contrast agent that is imaged by the magnetic resonance imaging apparatus;
        wherein the common agent includes a carrier including the first and second components;
    exciting magnetic resonance in selected dipoles of the subject and the first component of the common agent;
    with the magnetic imaging apparatus, detecting the magnetic resonance in the first component of the common agent and the selected dipoles of the subject;
    with the PET imaging apparatus, detecting radiation indicative of radioactive decay events of the second component of the common agent with a detector array;

reconstructing the detected magnetic resonance and the radiation into an image representation of the subject; and displaying the image representation.

5. The method as set forth in claim 4, further including: simultaneously performing the steps of detecting the magnetic resonance and detecting radiation.

6. A medical imaging apparatus comprising:
a magnetic resonance imaging apparatus including:
a main magnetic coil assembly configured to generate a main magnetic field in an imaging region of the apparatus,
a gradient coil assembly configured to overlay gradient magnetic fields on the main magnetic field, and
an RF coil assembly configured to transmit RF signals into the imaging region and detect magnetic resonance to produce detected magnetic resonance data;
a PET imaging apparatus including:
a detector array configured to detect radiation indicative of nuclear decay events;
at least one processor configured to:
produce an image representation from detected signals originating from nuclear decay events in the imaging region and enhancing spatial resolution of the image representation with the detected magnetic resonance data to produce a reconstructed image representation, and
calculate a value of total observable activity occurring in a voxel of space within the imaging region; and
a combined dynamic contrast enhanced MRI and dynamic PET contrast agent configured for injection into a patient disposed in the imaging region, the contrast agent including:
a combined carrier including a fluorine-19 component which is imaged by the magnetic resonance imaging apparatus and a radiopharmaceutical including fluorine-18 which decays to generate the nuclear decay events detected by the PET imaging apparatus,
a targeting system that takes advantage of biological processes to cause the contrast agent to collect in a target region, and
a dynamic contrast enhanced magnetic resonance imaging contrast (DCE-MRI) agent; and
a display for displaying the reconstructed image representation.

7. The medical imaging apparatus as set forth in claim 6, wherein the at least one processor is further configured to calculate the value of total observable activity, $Q_{OBS}(t)$, with the relationship:

$$Q_{OBS}(t)=(1-\beta)V_{EES}[C_{EES}(t)+C_T(t)]+\beta V_{EES}C_P(t)$$

where $V_{EES}$ is a volume of extracellular, extravascular space within a voxel, $\beta$ is a blood volume fraction, $C_T$ is a concentration of the contrast agent bound in the volume $V_{EES}$, $C_{EES}$ is a concentration of the contrast agent unbound within the volume $V_{EES}$, and $C_P$ is a plasma input function.

8. The medical imaging apparatus as set forth in claim 6, wherein the at least one processor is further configured to calculate a compartmental topology of the voxel with the differential relationships:

$$\frac{dC_{EES}(t)}{dt} = -(k_2+k_3)C_{EES}(t)+k_4C_T(t)+\frac{k_1C_P(t)}{V_{EES}}$$

$$\frac{dC_T(t)}{dt} = k_3C_{EES}(t)-k_4C_T(t)$$

where $k_1$ is a flow from a capillary into the extracellular, extravascular space, $k_2$ is a flow from the extracellular, extravascular space into the capillary, $k_3$ is a change of the contrast agent from the unbound state to the bound state within the extracellular, extravascular space, $k_4$ is the change of the contrast agent from the bound state to the unbound state within the extracellular, extravascular space, $V_{EES}$ is a volume of extracellular, extravascular space within the voxel, $C_T$ is a concentration of the contrast agent bound in the volume $V_{EES}$, $C_{EES}$ is a concentration of the contrast agent unbound within the volume $V_{EES}$, and $C_P$ is a plasma input function.

9. The medical imaging apparatus as set forth in claim 6, wherein the at least one processor is configured to calculate the value of total observable activity, $Q_{OBS}(t)$, with the relationship:

$$Q_{OBS}(t)=(1-\beta)V_{EES}[C_{EES}(t)+C_T(t)]+\beta V_{EES}C_P(t)$$

and wherein the at least one processor is further configured to calculate a compartmental topology of the voxel with the differential relationships:

$$\frac{dC_{EES}(t)}{dt} = -(k_2+k_3)C_{EES}(t)+k_4C_T(t)+\frac{k_1C_P(t)}{V_{EES}}$$

$$\frac{dC_T(t)}{dt} = k_3C_{EES}(t)-k_4C_T(t)$$

where $V_{EES}$ is a volume of extracellular, extravascular space within the voxel, $\beta$ is the blood volume fraction, $C_T$ is a concentration of the contrast agent bound in the volume $V_{EES}$, $C_{EES}$ is a concentration of the contrast agent unbound within the volume $V_{EES}$, $C_P$ is a plasma input function, $k_1$ is a flow from a capillary into the extracellular, extravascular space, $k_2$ is a flow from the extracellular, extravascular space into the capillary, $k_3$ is a change of the contrast agent from the unbound state to the bound state within the extracellular, extravascular space, and $k_4$ is the change of the contrast agent from the bound state to the unbound state within the extracellular, extravascular space.

10. The medical imaging apparatus as set forth in claim 9, wherein the at least one processor is further configured to generate at least one parametric map illustrating flow gradients of at least one of $k_1$, $k_2$, $k_3$, and $k_4$.

11. The medical imaging apparatus as set forth in claim 6, wherein the DCE-MRI contrast agent includes gadolinium (Gd).

12. A diagnostic imaging apparatus for contrast enhanced imaging of a patient, the apparatus comprising:
a magnetic resonance imaging apparatus including:
a main magnetic coil assembly configured to generate a main magnetic field in an imaging region of the apparatus,
a gradient coil assembly configured to overlay gradient magnetic fields on the main magnetic field, and
an RF coil assembly configured to at least transmit RF signals into the imaging region and receive magnetic resonance signals from the imaging region;
a PET imaging apparatus including:

a detector array configured to detect nuclear decay events of fluorine-18 concurrently with the receiving of the magnetic resonance signals by the RF coil assembly;

at least one processor configured to produce an image representation from the detected nuclear decay events and from the received magnetic resonance signals;

a contrast agent configured for injection into a patient disposed in the imaging region, the contrast agent including:
- a first component imaged by the magnetic resonance imaging apparatus,
- a radiopharmaceutical, which includes fluorine-18 which decays to generate the nuclear decay events detected by the PET imaging apparatus, the fluorine-18 being detected by the PET imaging apparatus concurrently with receiving the magnetic resonance signal from the first component by the magnetic resonance imaging apparatus, and
- a targeting system that takes advantage of biological processes to cause the contrast agent to collect in a target region;

the at least one processor being further configured to:
compute a blood volume fraction β based on magnetic resonance imaging information in the image representation, and
calculate an amount of activity $Q_{OBS}(t)$ in a voxel in the produced image representation with the relationship:

$$Q_{OBS}(t)=(1-\beta)V_{EES}[C_{EES}(t)+C_T(t)]+\beta V_{EES}C_P(t)$$

where $V_{EES}$ is a volume of extracellular, extravascular space within the voxel, β is the blood volume fraction, $C_T$ is a concentration of the contrast agent bound in the volume $V_{EES}$, $V_{EES}$ is a concentration of the contrast agent unbound within the volume $V_{EES}$, and $C_P$ is a plasma input function; and a display configured to display the image representation with an indication of the activity $Q_{OBS}(t)$ in the voxels of the image representation.

13. The diagnostic imaging apparatus as set forth in claim 12, wherein the targeting system includes at least one of a monoclonal antibody that attaches to a certain type of cell wall and a fibrin-specific paramagnetic nanoparticle.

14. The diagnostic imaging apparatus as set forth in claim 12, wherein the at least one processor is further configured to calculate a compartmental topology of the voxel with the differential relationships:

$$\frac{dC_{EES}(t)}{dt} = -(k_2+k_3)C_{EES}(t)+k_4C_T(t)+\frac{k_1C_P(t)}{V_{EES}}$$

$$\frac{dC_T(t)}{dt} = k_3C_{EES}(t)-k_4C_T(t)$$

where $k_1$ is a flow from a capillary into the extracellular, extravascular space, $k_2$ is a flow from the extracellular, extravascular space into the capillary, $k_3$ is a change of the contrast agent from the unbound state to the bound state within the extracellular, extravascular space, and $k_4$ is the change of the contrast agent from the bound state to the unbound state within the extracellular, extravascular space.

15. The diagnostic imaging apparatus as set forth in claim 14, wherein the at least one processor is further configured to calculate a perfusion of the contrast agent into and out of the volume of extracellular, extravascular space from a temporal change in retention of the contrast agent in the volume of extracellular, extravascular space, the retention of the contrast agent in the volume of extracellular, extravascular space being calculated from the image representation.

16. The diagnostic imaging apparatus as set forth in claim 12, wherein the at least one processor is further configured to identify at least one region of neovasculature as a target for destruction as part of a malignancy treatment regimen.

17. The diagnostic imaging apparatus as set forth in claim 12, wherein the at least one processor is further configured to create a three-dimensional parameter map for use in one of diagnosis and treatment.

18. A method of diagnostic imaging comprising:
injecting a subject with a common PET/MRI agent including:
- a first component including fluorine-19 that is imaged by a magnetic resonance imaging apparatus,
- a second component that includes a radiopharmaceutical including fluorine-18 that is imaged by a PET imaging apparatus concurrently with the imaging of the first component by the magnetic resonance imaging apparatus,
- a targeting system that takes advantage of biological processes to cause the common agent to collect in a target region, and
- wherein the agent is a molecule which includes the fluorine-18, the fluorine-19 and the targeting system;

with a magnetic resonance imaging apparatus, exciting magnetic resonance in selected dipoles of the subject and the first component of the common agent;

with the magnetic imaging apparatus, detecting the magnetic resonance of the first component of the common agent and the selected dipoles of the subject;

with the PET imaging apparatus, detecting radiation indicative of radioactive decay events of the fluorine-18 of the second component of the common agent;

reconstructing the detected magnetic resonance and the detected radiation into an image representation of the subject; and displaying the image representation.

19. A diagnostic imaging apparatus comprising:
a magnetic resonance imaging (MRI) apparatus;
a positron emission tomographic (PET) imaging apparatus;
at least one reconstruction processor configured to produce an image representation of a patient from data from the MRI apparatus and the PET imaging apparatus; and
a common agent configured for injection into the patient, the common agent including a plurality of molecules, each molecule comprising:
- a carrier including a fluorine-18 radioactive PET tracer,
- a targeting system which causes each molecule to collect in a target region of the patient, and
- at least one of:
  - a payload including a dynamic contrast enhanced magnetic resonance imaging (DCE-MRI) contrast agent, and
  - the carrier further including a fluorine-19 component.

20. The diagnostic imaging apparatus as set forth in claim 19, wherein each of the molecules includes the DCE-MRI contrast agent.

21. The diagnostic imaging apparatus as set forth in claim 20, wherein the DCE-MRI contrast agent includes gadolinium (Gd).

22. The diagnostic imaging apparatus as set forth in claim 19, wherein each of the molecules includes the DCE-MRI contrast agent and the carrier includes the fluorine-19 component.

* * * * *